United States Patent [19]
Brown et al.

[11] Patent Number: 5,731,873
[45] Date of Patent: Mar. 24, 1998

[54] FLUORESCENT SPECTROPHOTOMETER SYSTEM WITH AUTOMATIC CALIBRATION AND IMPROVED OPTICS BLOCK

[75] Inventors: Craig W. Brown; Paul Danilchik, both of Seattle, Wash.

[73] Assignee: Brooks Rand Ltd., Seattle, Wash.

[21] Appl. No.: 729,535

[22] Filed: Oct. 11, 1996

Related U.S. Application Data

[63] Continuation of Ser. No. 271,528, Jul. 7, 1994, abandoned.

[51] Int. Cl.$^6$ .................................................. G01N 21/01
[52] U.S. Cl. ............................................ 356/244; 356/326
[58] Field of Search ........................... 356/244, 435,
356/414, 334, 417, 320, 319, 411, 318,
246, 301, 440, 328, 308, 305, 323, 325,
326; 250/458.1, 459.1, 461.1, 462.2

[56] References Cited

U.S. PATENT DOCUMENTS

| | | | |
|---|---|---|---|
| 4,158,505 | 6/1979 | Mathisen et al. | 356/308 |
| 4,279,506 | 7/1981 | Maines | 356/244 |
| 4,750,837 | 6/1988 | Gifford et al. | 356/318 |
| 5,305,093 | 4/1994 | Dosmann | 356/435 |

OTHER PUBLICATIONS

Description and Specifications of the Brooks Rand Cold Vapor Atomic Fluorescence Spectrophotometer, No date.
Summary page entitled AD7712 on Self Calibration, System Calibration, System Offset Calibration, Background Calibration, and Span and Offset Limits, Rev. B No date.
Operational Manual for CVAFS–2 Mercury Analyzer, by Brooks Rand, Ltd., dated Nov. 1, 1990, pp. 1–29.
Description, Specifications, and Technical Data of HC120 Series, ½ Inch Side–on PMT Detector Assembly, Hamamatsu Corporation, Revised Sep. 1991, 4 pages.

*Primary Examiner*—K. Hantis
*Attorney, Agent, or Firm*—Marshall, O'Toole, Gerstein, Murray & Borun

[57] ABSTRACT

A spectrophotometer system includes an optics block housing an excitation lamp and a cell for receiving a gas to be detected. The excitation lamp excites atoms of the gas to be detected to produce photons. The spectrophotometer system also includes a photo-multiplier tube assembly and an analog-to-digital converter. The photo-multiplier tube assembly detects the photons, and produces an analog output accordingly. The analog-to-digital converter converts this analog output to a digital output. The photo-multiplier tube assembly and the analog-to-digital converter of a spectrophotometer system are calibrated together so that a zero input to the analog-to-digital converter may be defined as an absence of photons. The optics block is configured to minimize scattering of light, without a lens, so that the output of the spectrophotometer system is a function of the number of atoms of the gas to be detected and not of scattered light.

43 Claims, 5 Drawing Sheets

FLUORESCENT SPECTROPHOTOMETER SYSTEM WITH AUTOMATIC CALIBRATION AND IMPROVED OPTICS BLOCK

This is a continuation of U.S. application Ser. No. 08/271,528, filed Jul. 7, 1994, now abandoned.

TECHNICAL FIELD OF THE INVENTION

The present invention relates to a spectrophotometer system having automatic zero offset calibration of an analog-to-digital converter and having an optics block which is arranged to reduce lamp to detector light scattering.

BACKGROUND OF THE INVENTION

A fluorescent spectrophotometer may be used, for example, to detect whether atoms of a specific gas are present in a gas sample. In a typical fluorescent spectrophotometer, the gas sample to be analyzed is mixed with an inert gas and the resulting gas mixture is flowed through a cell of the fluorescent spectrophotometer. As the gas mixture flows through the cell, light from a light source is directed to the cell in order to excite atoms of the gas to be detected if these atoms are present in the gas mixture.

In order to determine if the gas sample includes atoms of the gas to be detected, the light source is selected so that its emitted light has a predetermined wavelength. This predetermined wave-length is chosen so that atoms of the gas to be detected are excited to the point that they emit photons as these atoms return from their excited state to their ground state. Consequently, if the gas sample in the gas mixture flowing through the cell contains atoms of the gas to be detected, the light from the light source raises the electrons of these atoms to increased energy states. As these electrons return to their ground state, they emit photons.

These photons are passed through a narrow bandpass optical filter which is arranged to have a frequency passband generally centered on the frequency of the emitted photons. A light amplifier, such as a photomultiplier tube, amplifies the photons and supplies an output voltage signal which is indicative of the number of photons received by the light amplifier. Thus, this output voltage signal gives an indication of the number of atoms of the gas to be detected which are present in the gas sample at any instant in time.

A fluorescent spectrophotometer may be used, for example, to detect the level of gaseous mercury in a gas sample. If so, an excitation lamp, with a low pressure mercury vapor therein, is selected to supply light to the gas sample to be analyzed. The light emitted by this lamp has a wavelength of about 253.7 nanometers. If mercury atoms are present in the gas sample, the mercury atoms are excited by the light from the excitation lamp. The excited mercury atoms emit photons also having a wavelength of about 253.7 nanometers. These photons are passed through the narrow bandpass optical filter having a frequency passband such that photons having a wavelength of mercury, 253.7 nanometers, pass through the filter.

The photons passing through the filter are detected by a photo-multiplier tube assembly of the fluorescent spectrophotometer. The photo-multiplier tube assembly includes a photo-multiplier tube which produces a current in response to the photons. The photomultiplier tube assembly also includes a current-to-voltage conversion amplifier which converts the current to an analog output voltage. The level of the analog output voltage gives an indication of the number of mercury atoms in the gas sample. The analog output voltage from the current-to-voltage conversion amplifier of the photo-multiplier tube assembly is converted to a digital quantity by an analog-to-digital converter. This digital quantity is then processed by a microprocessor which can provide a local display of the mercury level in the gas sample and/or can drive a modem for transmitting an indication of the mercury level in the gas sample to a remote point or to a local computer.

There have been a number of problems with existing fluorescent spectrophotometers. For example, the digital quantity provided by the analog-to-digital converter to the microprocessor of the spectrophotometer system can include error from at least two sources. One source of error is the current-to-voltage conversion amplifier typically used in a photomultiplier tube assembly. This current-to-voltage conversion amplifier can have an output offset voltage even when the excitation lamp of the fluorescent spectrophotometer is off. Accordingly, although the analog output voltage of the photomultiplier tube assembly should be at zero when the lamp of the fluorescent spectrophotometer is off, the photomultiplier tube assembly actually produces an analog output voltage equal to the output offset voltage of the current-to-voltage conversion amplifier.

Another potential source of error in the digital quantity provided by the analog-to-digital converter to the microprocessor of the spectrophotometer system is the method used to calibrate the analog-to-digital converter. In general, an analog-to-digital converter is supposed to provide a zero output when its input is zero, and is supposed to have a predetermined relationship between its output range and a given input range. Thus, both the zero point and the range of an analog-to-digital converter are normally calibrated. Zero offset calibration of the analog-to-digital converter requires establishing a zero reference level for the input of the analog-to-digital converter.

Several different calibration techniques have been employed in the past for zero offset calibration of an analog-to-digital converter. For example, in one such technique, the analog-to-digital converter creates an internal short circuit between its analog input and an internal ground to thereby establish a zero input level. The analog-to-digital converter is adjusted until its digital output is also zero. This zero offset calibration, however, is itself subject to an ill defined offset error. That is, although the digital output voltage of the analog-to-digital converter should be zero when its analog input is connected to the internal ground of the analog-to-digital converter, the analog-to-digital converter actually produces a digital output voltage equal to the offset error of the analog-to-digital converter. This offset error is referred to herein as zero offset error.

Furthermore, a fluorescent spectrophotometer typically includes an optics block which may also be a source of error. This optics block provides a light path for directing the light from the excitation lamp to the cell, a light path for directing the photons emitted by the atoms of the gas to be detected from the cell to the photomultiplier tube assembly, and a gas path for conducting the flow of the gas mixture to and from the cell. This optics block is typically made of anodized aluminum.

Anodized aluminum is chosen for the optics block because it is a relatively good absorber of light and, therefore, suppresses the scattering of light off of the walls of the light paths which transmit the light from the excitation lamp to the cell and which transmit the photons from the cell to the photomultiplier tube assembly. That is, the photomultiplier tube assembly ideally measures only the light emitted as photons from the excited atoms of the gas to be detected.

However, light from the excitation lamp may be scattered by the optics block and cell. If this scattered light reaches the photomultiplier tube, the scattered light spuriously adds to the photons from the excited atoms of the gas to be detected to produce an error in the output of the photomultiplier tube assembly. If so, the output of the photomultiplier tube assembly is a function not only of the photons emitted by the atoms of the gas to be detected, but also of the scattered light.

If the intensity of the scattered light were constant, light scattering would not necessarily be a limitation on the detection sensitivity of the fluorescent spectrophotometer. Thus, the assumed constant intensity of the scattered light could be measured in the absence of emitted photons, and the measured intensity of the scattered light could be simply subtracted from the output of the photomultiplier tube assembly during analysis of a gas sample. The output of the fluorescent spectrophotometer would then be a function of only the number of atoms of the gas to be detected. In other words, if the scattered light intensity is known with complete certainty, the light intensity which is above the background intensity caused by light scattering must be due only to the emission of photons from the atoms of the gas to be detected.

However, in a typical fluorescent spectrophotometer, the scattered light intensity cannot be precisely characterized since it fluctuates about some value. These fluctuations are due, at least in part, to fluctuations in the excitation lamp, and fluctuations in the excitation lamp in turn results in fluctuations in the intensity of the light emitted by the lamp.

SUMMARY OF THE INVENTION

The present invention overcomes one or more of these problems by calibrating the photomultiplier tube assembly and the analog-to-digital converter of a spectrophotometer system together and/or by dimensioning the optics block to minimize the amount of scattered light. By calibrating the photomultiplier tube assembly and the analog-to-digital converter of a spectrophotometer system together, a zero input to the analog-to-digital converter may be defined as the point at which no photons could be emitted by a gas sample. Accordingly, both the current-to-voltage conversion amplifier of the photomultiplier tube assembly and the analog-to-digital converter are calibrated in one operation, and the zero offset of the analog-to-digital converter is referenced to the physical condition being detected. Furthermore, the optics block may be dimensioned so that the amount of scattered light reaching the photon detector is minimized. Thus, the output of the fluorescent spectrophotometer is a function primarily of the number of atoms of the gas to be detected.

Therefore, in accordance with one aspect of the present invention, an apparatus for calibrating an analog-to-digital converter includes a detector having an input and an output, an analog-to-digital converter having an analog input connected to the output of the detector and having a digital output, and a calibration controlling means connected to the input of the detector and to the analog-to-digital converter for controlling calibration of the analog-to-digital converter at a preconditioned level of signal on the input of the detector.

In accordance with another aspect of the present invention, a light transmitter for use in a spectrophotometer includes first and second light paths of substantially light absorbing material and a cell. The first light path has first and second ends. The first end of the first light path is arranged to receive light. The cell is in light receiving communication with the second end of the first light path, and is arranged to receive a gas sample to be analyzed. The second light path has first and second ends. The first end of the second light path is in light receiving communication with the cell. The light transmitter is dimensioned to inhibit light from the first end of the first light path entering the first end of the second light path.

In yet another aspect of the present invention, a system for analyzing a sample includes a spectrophotometer having an input and an output, wherein the spectrophotometer receives the sample to be analyzed, wherein the spectrophotometer stimulates the sample in response to an input signal on its input, and wherein the spectrophotometer provides an analog signal on its output which is dependent upon the stimulated sample. An analog-to-digital converter has an input and an output, wherein the input of the analog-to-digital converter is connected to the output of the spectrophotometer so as to receive the analog signal on the output of the spectrophotometer, and wherein the analog-to-digital converter converts the analog signal to a digital signal. A processor is connected to the input of the spectrophotometer and to the analog-to-digital converter. The processor processes the digital signal so as to analyze the sample and controls calibration of the analog-to-digital converter at a preconditioned level of the input signal on the input of the spectrophotometer.

In a further aspect of the present invention, a system for analyzing a sample includes a light source. A first path of substantially light absorbing material has first and second ends, and the first end of the first light path is arranged to receive light from the light source. A cell is in light receiving communication with the second end of the first light path, and the cell receives the sample to be analyzed. A second light path of substantially light absorbing material has first and second ends, and the first end of the second light path is in light receiving communication with the cell. The first light path and the cell are dimensioned to inhibit light from the first end of the first light path entering the first end of the second light path. A detecting means detects light at the second end of the second light path, and the detecting means has an output for providing an output signal representing the detected light. A processing means is connected to the light source and to the output of the detecting means for processing the output signal of the detecting means so as to analyze the sample.

BRIEF DESCRIPTION OF THE DRAWING

These and other features and advantages of the present invention will become more apparent from a detailed consideration of the invention when taken in conjunction with the drawing in which.

DETAILED DESCRIPTION OF THE INVENTION

Figure 1A:
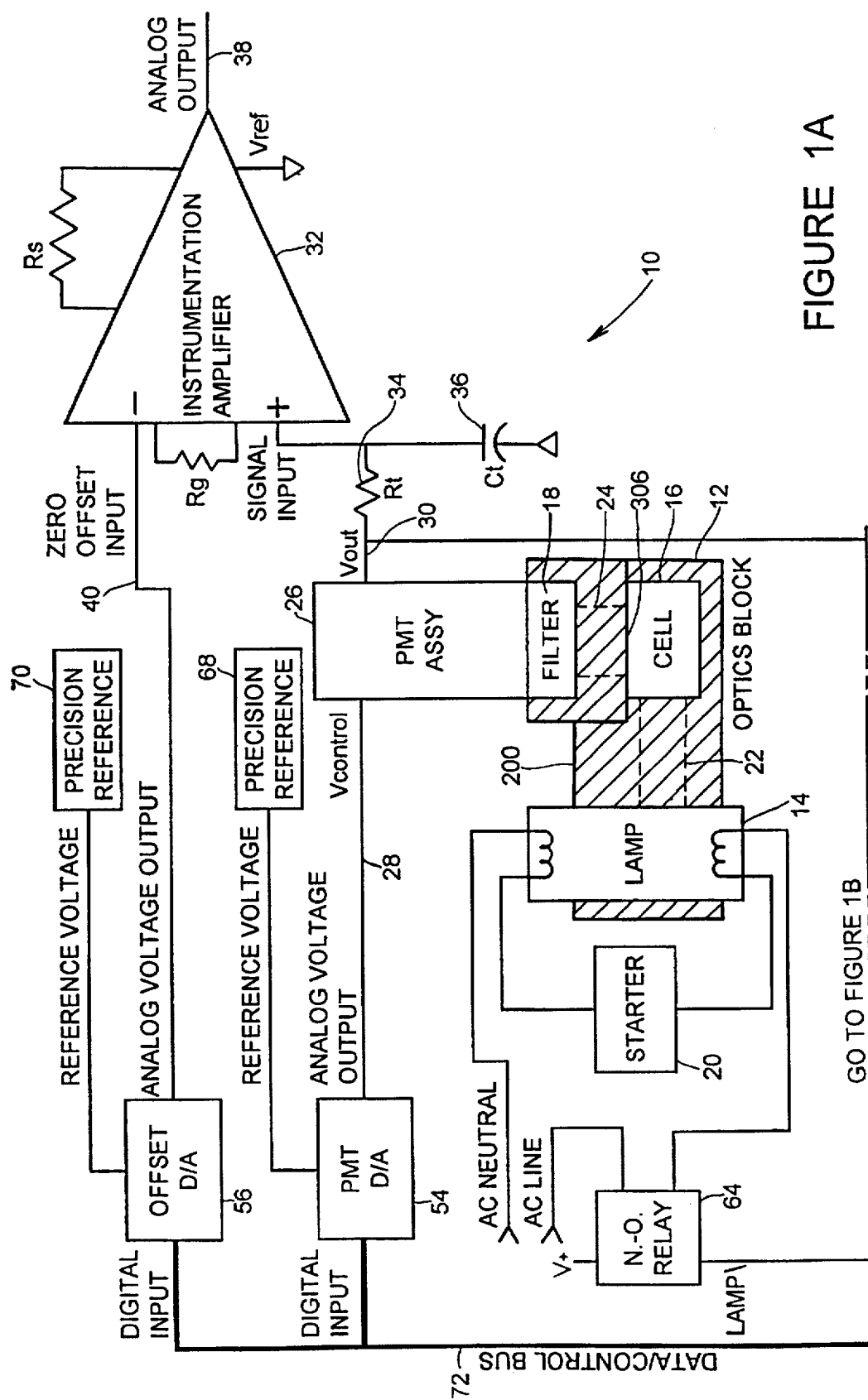
FIGS. 1A–B is a block diagram of a fluorescent spectrophotometer system according to the present invention.

As shown in FIG. 1, a fluorescent spectrophotometer system 10 includes an optics block 12 having an excitation fluorescent lamp 14, a cell 16, and an optical filter 18. The optics block 12 may be fabricated from anodized aluminum which serves as protection against acidic environments and also as a light absorber to suppress light scattering. The cell 16 may be fabricated from quartz. As is typical with fluorescent lamps, the excitation fluorescent lamp 14 has a starter 20 associated therewith.

The cell 16 is arranged to receive a gas sample to be analyzed. Light from the excitation fluorescent lamp 14 is transmitted to the cell 16 by a first light path 22 of the optics block 12. Atoms of a gas to be detected are excited by the light transmitted to the cell 16 through the first light path 22 and consequently emit photons if such atoms are in the gas sample flowing through the cell 16. These photons are transmitted by a second light path 24 from the cell 16 to the optical filter 18. The first and second light paths 22 and 24 may be bores which are machined into the optics block 12. The optical filter 18 has a narrow bandpass with a center frequency substantially equal to the frequency of the photons emitted by the atoms of the gas to be detected.

The photons, which are emitted by atoms of the gas to be detected in the gas sample supplied to the cell 16 of the optics block 12 and which are filtered by the optical filter 18, are converted to a current and the current is amplified by a photomultiplier tube of a photomultiplier tube assembly 26. Besides the photomultiplier tube, the photomultiplier tube assembly 26 also comprises a power supply and a linear current-to-voltage conversion amplifier. The photomultiplier tube assembly 26 may be, for example, an HC120 series detector assembly supplied by Hamamatsu Corporation.

The power supply of the photomultiplier tube assembly 26 produces a high voltage across the photomultiplier tube based upon a voltage on an input line 28 of the photomultiplier tube assembly 26. The linear current-to-voltage conversion amplifier of the photomultiplier tube assembly 26 produces an analog output voltage based upon the current generated by the photomultiplier tube of the photomultiplier tube assembly 26. This analog output voltage is provided on an output line 30.

The fluorescent spectrophotometer system 10 may include a precision amplifier 32 which, as shown, is connected as an integrator having a time constant determined by a resistor 34 and a capacitor 36. The precision amplifier 32 provides, on an output line 38, an analog output which is the difference between the analog output voltage on the output line 30 from the photomultiplier tube assembly 26 and a reference voltage. This reference voltage is supplied to the precision amplifier 32 over an input line 40. The precision amplifier 32 may be, for example, an amplifier supplied under the generic part number AMP01.

The output line 30 of the photomultiplier tube assembly 26 is also connected as an analog input to an analog-to-digital converter 42. The analog-to-digital converter 42 operates under control of a microprocessor 44 by way of a control bus 46, and provides a digital output to the microprocessor 44 over a data line 48. The analog-to-digital converter 42 is a charge balancing type of converter which is suitable for integrating the slowly changing signal on the output line 30 of the photomultiplier tube assembly 26. The integration rate of the analog-to-digital converter 42 is determined by the frequency o a clock signal provided by a master clock 50 and by a digital filter which is internal to the analog-to-digital converter 42. The processing rate of the microprocessor 44 is determined also by the master clock 50. The analog-to-digital converter 42 may be, for example, an AD7712 analog-to-digital converter supplied by Analog Devices; and the microprocessor 44 may be, for example, an 68HC11E9 microprocessor supplied by Motorola. The SCK terminal of the microprocessor 44 provides a serial clock signal to synchronize the transmission of data from the analog-to-digital converter 42 over the data line 48 to the serial data port of the microprocessor 44.

The output impedance of the current-to-voltage conversion amplifier of the photomultiplier tube assembly 26 is low, and the input impedance of the precision amplifier 32 is high. Therefore, there is little impedance loading on the input of the analog-to-digital converter 42 with respect to the analog output voltage on the output line 30. Since there is little impedance loading on the input of the analog-to-digital converter 42, any error introduced by this impedance loading is well within the existing errors of the measurement system.

The analog-to-digital converter 42 samples its analog input during an integration period, and converts the sampled analog input to a digital output at the end of this integration period. At the end of the integration period, the analog-to-digital converter 42 also supplies an interrupt over the control bus 46 to the microprocessor 44. In response to this interrupt, the microprocessor 44 reads the digital output on the data line 48 while the analog-to-digital converter 42 begins the next integration period.

If desired, the microprocessor 44 may employ a many-word finite impulse response (FIR) filter in order to filter the digital output received from the analog-to-digital converter 42 over the data line 48. The microprocessor 44 provides the filtered digital output to a display 52. The display 52 may be, for example, a LM40255 display supplied by Sharp Corporation.

The display 52 may be divided into a plurality of segments. A first segment of the display 52 may be used to display the photomultiplier tube input voltage which is supplied on the input line 28 by a digital-to-analog converter 54, a second segment of the display 52 may be used to display the instantaneous results of conversions by the analog-to-digital converter 42, a third segment of the display 52 may be used to display a peak conversion result of the analog-to-digital converter 42, and a fourth segment of the display 52 may be used to display an output offset value which is supplied by a digital-to-analog converter 56 to the input line 40 of the precision amplifier 32.

The peak conversion result displayed by the third segment of the display 52 is obtained during the analog-to-digital conversion of the output from the photomultiplier tube assembly 26. That is, as each digital output on the data line 48 from the analog-to-digital converter 42 is read by the microprocessor 44, it is compared to the previous peak value of the digital output provided by the analog-to-digital converter 42. If the new value is larger than the previous peak value, the new value is stored as the peak value. If the new value is not larger than the previous peak value, the new value is not stored as the peak value. At the end of a sampling cycle, therefore, the peak value displayed by the third segment of the display 52 is the largest digital quantity read from the analog-to-digital converter 42 during the sampling cycle, and represents the largest output on the output line 30 from the photomultiplier tube assembly 26. This largest output corresponds to the highest concentration of the atoms of the gas to be detected in the gas sample within the cell 16 during the sampling cycle.

At the beginning of each sampling cycle, the peak value of the previous sampling cycle is reset by operation of a corresponding key on a keypad 58. The keypad 58 is provided so that a user may manually control the microprocessor 44. The keypad 58 may be arranged to have four keys (i.e., switches). Operation of a first key of the keypad 58 merely resets the peak value on the display 52. Operation of a second key of the keypad 58 establishes an output offset value provided by the digital-to-analog converter 56 on the input line 40 of the precision amplifier 32. This output offset value is also used by the FIR filter of the microprocessor 44. Consequently, this output offset value is subtracted from subsequent FIR filtered outputs of the analog-to-digital converter 42 to be displayed by the display 52. Thus, the current output of the fluorescent spectrophotometer system 10, both as displayed by the display 52 and as provided by the precision amplifier 32 on the output line 38, is the actual output from the photomultiplier tube assembly 26 minus the output offset value provided by the digital-to-analog converter 56.

The keypad 58 may also include third and fourth keys. Each of these two keys has three functions. The third key of the keypad 58 increases the voltage applied by the digital-to-analog converter 54 to the input line 28 of the photomultiplier tube assembly 26, and the fourth key decreases this voltage. Accordingly, these third and fourth keys of the keypad 58 increase or decrease the sensitivity of the detector to light, as may be required to compensate for changes in the intensity of the excitation fluorescent lamp 14 with time. Both the third and fourth keys of the keypad 58 also reset the peak value which is displayed on the display 52, and both reset the output offset provided by the digital-to-analog converter 56 to zero in order to allow the sensitivity of the fluorescent spectrophotometer system 10 to background scattering of the optics block 12 to be gauged by observing the output on the output line 30 of the photomultiplier tube assembly 26.

The microprocessor 44 is connected to an RS232 port 60 through an RS232 driver/receiver 62 so that the microprocessor 44 can communicate with a remote terminal or a local computer such as a PC. The microprocessor 44 controls the energization state of the excitation fluorescent lamp 14 by way of a normally open relay 64. Precision references 66, 68, and 70 may be provided in order to calibrate the ranges of the analog-to-digital converter 42, the digital-to-analog converter 54, and the digital-to-analog converter 56.

In order to eliminate the zero offset errors of the current-to-voltage conversion amplifier of the photomultiplier tube assembly 26 and of the analog-to-digital converter 42, the analog-to-digital converter 42 is calibrated while the excitation fluorescent lamp 14 is deenergized, while the voltage on the input line 28 of the photomultiplier tube assembly 26 is zero, and while the analog output voltage on the output line 30 is sampled. That is, this calibration process is accomplished with zero volts on the input line 28 of the photomultiplier tube assembly 26 and by controlling the normally open relay 64 so as to deenergize the excitation fluorescent lamp 14.

While zero volts are on the input line 28 of the photomultiplier tube assembly 26 and while the excitation fluorescent lamp 14 is deenergized, the analog-to-digital converter 42 is calibrated. The analog-to-digital converter 42 has a plurality of calibration modes. Although any of the calibration modes of the analog-to-digital converter 42 may be implemented in connection with the present invention, the mode implemented by the preferred embodiment of the present invention is the system offset calibration mode. In this mode, calibration is initiated by the microprocessor 44 following which the analog-to-digital converter 42 uses the signal level on its input, while zero volts are on the input line 28 of the photomultiplier tube assembly 26 and while the excitation fluorescent lamp 14 is deenergized, to determine a system zero scale coefficient. The analog-to-digital converter 42 then adjusts an internal filter by use of this system zero scale coefficient so that its digital output when analyzing a gas to be detected is compensated for any offset error. Alternatively, the microprocessor 44 could itself perform calibration of the analog-to-digital converter 42 by reading the digital output of the analog-to-digital converter 42 during zero offset calibration and by directly controlling the analog-to-digital converter 42 until its digital output is zero. As a further alternative, the microprocessor 44 could perform calibration of the analog-to-digital converter 42 by reading the digital output of the analog-to-digital converter 42 during zero offset calibration and by storing and subtracting this output from future readings of the digital output of the analog-to-digital converter 42.

By controlling the voltage on the input line 28 at zero volts, the microprocessor 44 ensures that the smallest possible current input is provided on the input line 28 to the current-to-voltage conversion amplifier of the photomultiplier tube assembly 26. By deenergizing the excitation fluorescent lamp 14, the microprocessor 44 ensures that, even if zero volts on the input line 28 of the photomultiplier tube assembly 26 can still generate some very small response to photons, there are no photons being produced as a result of illumination by the excitation fluorescent lamp 14. In this way, a zero reference is provided to the analog-to-digital converter 42 which is based on the condition (i.e., atoms of the gas to be detected) being sensed.

Accordingly, the calibration of the analog-to-digital converter 42 to have a zero offset error is referenced to the condition being sensed, i.e. the analog-to-digital converter 42 is calibrated under conditions which assure that the output of the photomultiplier tube assembly 26 indicates the presence of no atoms of the gas to be detected. Thus, offset errors of the current-to-voltage conversion amplifier of the photomultiplier tube assembly 26 and offset calibration errors internal to the analog-to-digital converter 42 do not contribute to the output of the analog-to-digital converter 42 as it relates to the condition sensed by the fluorescent spectrophotometer system 10.

Before the fluorescent spectrophotometer system 10 analyzes a sample of gas in the cell 16, or periodically, the microprocessor 44 is initialized according to an initialization routine stored therein. During execution of this initialization routine, the microprocessor 44 maintains the normally open relay 64 open so that the excitation fluorescent lamp 14 is deenergized, the microprocessor 44 writes a zero over a data control bus 72 to the digital-to-analog converter 54 so that the voltage on the input line 28 of the photomultiplier tube assembly 26 is at a zero level, and the microprocessor 44 prompts the analog-to-digital converter 42 over the control bus 46 to calibrate itself for zero offset error. Therefore, the output of the analog-to-digital converter 42 should indicate no gas to be detected, i.e. the output of the analog-to-digital converter 42 should be zero. Also, the precision reference 66 may be used to calibrate the range of the analog-to-digital converter 42, as is known. The display 52 may have an additional segment in order to provide an indication that the fluorescent spectrophotometer system 10 is being initialized.

After initialization by the microprocessor 44, but before supplying a gas sample to the cell 16, the user may desire to adjust the sensitivity of the fluorescent spectrophotometer system 10 to yield a signal on the output 30, for example, on the order of three-fourths full scale. Accordingly, the microprocessor 44 energizes the excitation fluorescent lamp 14 through the normally open relay 64. The user then presses the third key of the keypad 58 to increase the digital word supplied over the data control bus 72 to the digital-to-analog converter 54 which, in turn, increases the voltage on the input line 28. Pressing of the third key of the keypad 58 also resets the peak value on the third segment of the display 52 and resets the output offset value supplied by the digital-to-analog converter 56 to the input line 40 of the precision amplifier 32. As the voltage on the input line 28 increases, the output on the output line 30, and consequently the output of the analog-to-digital converter 42, increases. The user may watch the increase of the output of the analog-to-digital converter 42 on the second segment of the display 52. When the output of the analog-to-digital converter 42 reaches three-fourths of full scale, for example, the third key of the keypad 58 is released.

Since the gas sample, at this point, has not yet been supplied to the cell 16, the output on the output line 30 from the photomultiplier tube assembly 26 is due only to background scattering. (That is, even though the optics block 12 is configured to minimize background scattering, some background scattering may still exist.) Since the output offset value on the input line 40 at this point is at zero volts and is subtracted from the FIR filtered conversion results of the analog-to-digital converter 42 as displayed by the display 52, the display 52 now displays (i) the input voltage on the input line 28 of the photomultiplier tube assembly 26 on its first segment, (ii) the instantaneous background scattering signal from the photomultiplier tube assembly 26 on its second segment, (iii) the peak value of the background scattering signal above its average value on its third segment, and (iv) zero as the output offset voltage on its fourth segment.

Also before a gas sample is supplied to the cell 16, the user operates the second key of the keypad 58 to adjust the voltage to the digital-to-analog converter 56 in order to drive the output on the output line 38 to zero. The output line 38 may be connected to a display, such as a chart recorder, for this purpose. The amount of input to the digital-to-analog converter 56 required to drive the output on the output line 38 to zero is then saved by the microprocessor 44 as a stored output offset. This amount represents the contribution of background scattering which may exist in the optics block 12. The stored output offset is subtracted from the conversion results of the analog-to-digital converter 42, which represents the analog output of the photomultiplier tube assembly 26, in order to subtract out any contribution of background scattering from the measured output of the photomultiplier tube assembly 26. Thus, the first segment of the display 52 shows the voltage on the input line 28 of the photomultiplier tube assembly 26, the second segment of the display 52 shows a value that fluctuates about zero, and the fourth segment of the display 52 shows a fixed output offset value equal to the stored output offset representing background scattering.

At this point, with the excitation fluorescent lamp 14 energized through the normally open relay 64, the user may now run a gas sample through the cell 16 in order to begin normal continuous analog-to-digital conversion of the output of the photomultiplier tube assembly 26 on the output line 30. Once normal analog-to-digital conversions are occurring, the display 52 displays the conversion results of the analog-to-digital converter 42, the photomultiplier tube input voltage on the input line 28, and other information relevant to the performance of the fluorescent spectrophotometer system 10.

As an example, the present invention may be used to detect the amount of mercury in a gas flow, such as the combustion gas produced by burning fossil fuels. If so, the excitation fluorescent lamp 14 is chosen so that its fluorescing gas is mercury in order to produce light having a wavelength which will cause mercury atoms in the gas sample to emit photons. AS the number of mercury atoms in the gas sample flowing through the cell 16 increases, the number of photons received by the photomultiplier tube assembly 26 consequently increases. As the number of mercury atoms in the gas sample flowing through the cell 16 decreases, the number of photons received by the photomultiplier tube assembly 26 consequently decreases. The changing number of photons results in a corresponding change in the output on the output line 30 of the photomultiplier tube assembly 26, and a corresponding change in the digital output on the data line 48 of the analog-to-digital converter 42. As the sample atoms flow through the system, a peak concentration in the gas sample in the cell 16 builds, is reached, and is passed. The peak amount of mercury, however, is saved as the concentration of the gas to be detected in the cell 16 varies. This peak value is displayed by the third segment of the display 52.

Figure 2:
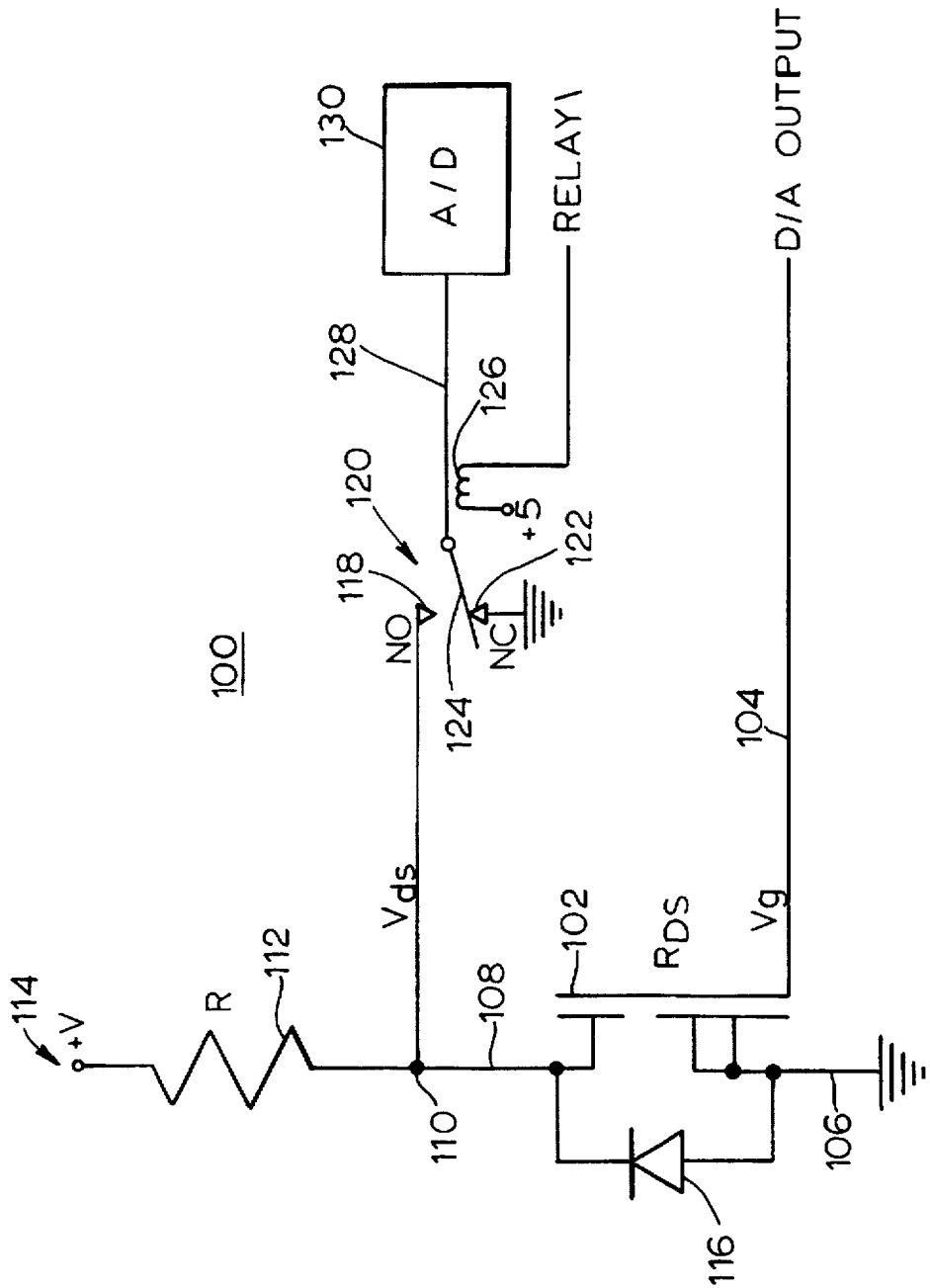
FIG. 2 illustrates an alternative calibration implementation according to the present invention.

The calibration procedure of the present invention is also useful in conjunction with a detector 100 as shown in FIG. 2. The detector 100 includes an amplifier 102, which may be a MOSFET, having a gate terminal 104, a source terminal 106 connected to ground, and a drain terminal 108 connected to a junction 110. The amplifier 102 is controlled by a voltage $V_g$ on the gate terminal 104, and the amplifier 102 has a drain to source resistance $R_{ds}$ between its drain terminal 108 and its source terminal 106. The junction 110 is connected through a resistor 112 to a voltage source 114. The resistor 112 has a predetermined resistance R, and the voltage source 114 has a predetermined voltage V. A diode 116 is forward connected from the source terminal 106 to the drain terminal 108 of the amplifier 102. The junction 110 is also connected to a normally open contact 118 of a relay 120. The relay 120 has a normally closed contact 122 which may be referred to as an input of the detector 100 and which is connected to ground. The relay 120 has a pole 124 which is controlled by a coil 126. The pole 124 is connected to an A/D input 128 of an analog-to-digital converter 130, which may be similar to the analog-to-digital converter 42, and the coil 126 is controlled by a microprocessor similar to the microprocessor 44.

The detector 100 as shown in FIG. 2 allows the analog-to-digital converter 130 to be calibrated, and allows the drain to source resistance $R_{ds}$ of the amplifier 102 to be characterized as a function of the gate voltage $V_g$ on the gate terminal 104 of the amplifier 102. During calibration, the relay 120 is operated by the coil 126 so that the pole 124 is against the normally closed contact 122. The A/D input 128 of the analog-to-digital converter 130 is, therefore, at ground potential, i.e. zero volts. Thus, the analog-to-digital converter 130 may be calibrated with its A/D input 128 at zero volts.

In this calibration procedure, it is important to use the relay 120 as described in order to ensure a zero input on the A/D input 128 of the analog-to-digital converter 130. Controlling the gate voltage $V_g$ on the gate terminal 104 of the amplifier 102 does not result in zero volts on the A/D input 128. That is, controlling the gate voltage $V_g$ so that it is zero results in a voltage $V_{ds}$ at the junction 110 near the voltage V of the voltage source 114. On the other hand, increasing the gate voltage $V_g$ until the amplifier 102 saturates results in a voltage $V_{ds}$ at the junction 110 which is above ground potential by an amount determined by the resistance $R_{ds}$ at saturation of the amplifier 102.

After zero offset calibration of the analog-to-digital converter 130, the pole 124 may be operated against the normally open contact 118 by the relay 120 so that the resistance ($R_{ds}$) versus voltage ($V_g$) characteristic curve of the amplifier 102 may be plotted. This curve may be plotted by use of the following equation:

$$R_{ds} = \frac{RV_{ds}}{(V - V_{ds})} \quad (1)$$

where the resistance R of the resistor 112 is known because it is predetermined, the voltage V of the voltage source 114 is known because it is predetermined, and the voltage $V_{ds}$ may be sampled at the output of the analog-to-digital convertor 130. By varying the gate voltage $V_g$ on the gate terminal 104 of the amplifier 102, and by using equation (1) above, the $R_{ds}$ versus $V_g$ characteristic curve for the amplifier 102 can be plotted.

Figure 5:
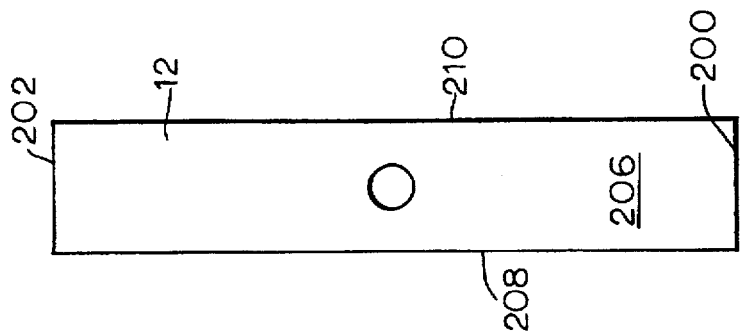
FIG. 5 is a third view of the optics block shown in FIG. 3.
Figure 3:
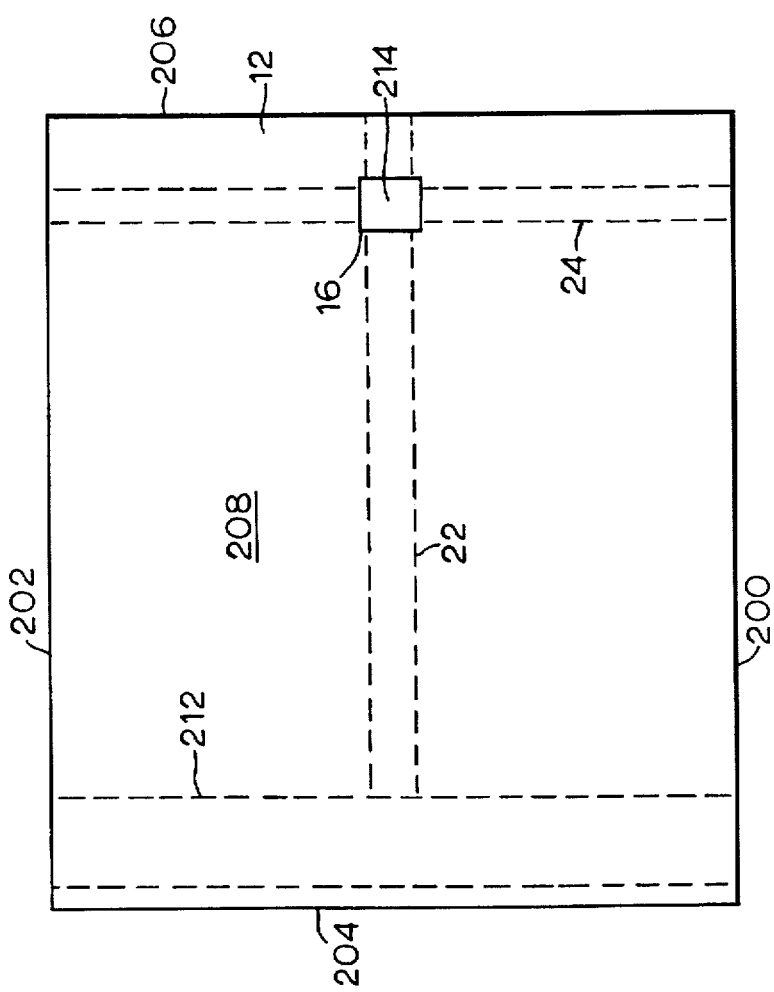
FIG. 3 is a first view of an optics block for use in the fluorescent spectrophotometer system shown in FIG. 1.
Figure 4:
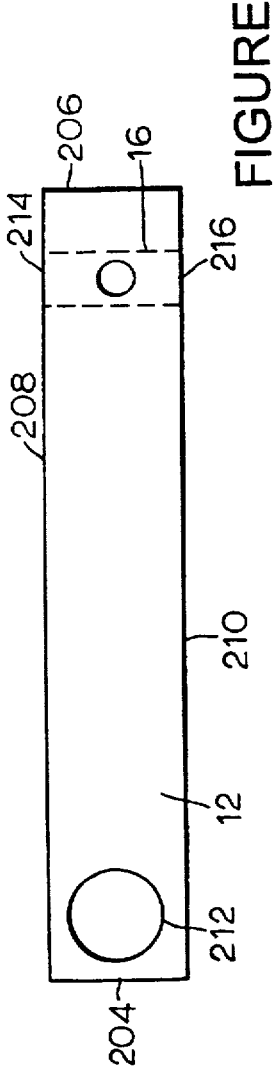
FIG. 4 is a second view of the optics block shown in FIG. 3.

The optics block 12 is shown in more detail in FIGS. 3 through 5. The optics block 12 is parallelopided in shape having sides 200, 202, 204, 206, 208, and 210. The optics block 12 has a bore 212 which extends through the optics block 12 between the side 200 and the side 202. The excitation fluorescent lamp 14 is inserted into the optics block 12 through the bore 212. Light from the excitation fluorescent lamp 14 in the bore 212 transmits along the first light path 22 to the cell 16. As light from the excitation fluorescent lamp 14 enters the cell 16, atoms f a gas to be detected in the cell 16 are excited and emit photons which are transmitted along the second light path 24 to the side 200. The number of emitted photons depends upon the number of emitting atoms which are in the cell 16. The optical filter 18 and the photomultiplier tube assembly 26, which are located at the side 200 of the optics block 12, detect the photons and produce a voltage dependent upon the number of emitted photons.

The cell 16 may be a square, rectangular sided quartz tube extending between the sides 208 and 210 of the optics block 12, and has open ends 214 and 216. Thus, as viewed in FIG. 3, the open end 214 of the cell 16 is in the shape of a square. Similarly, the open end 216 of the cell 16 is also in the shape of a square. The sides of the cell 16 between the open ends 214 and 216 are in the shape of rectangles. A gas sample is flowed through the cell 16 from one of the open ends 214 and 216 to the other.

The optics block 12 is arranged to minimize the amount of excitation light (i.e., light which is emitted by the excitation fluorescent lamp 14 in the bore 212) which reaches the optical filter 18 and photomultiplier tube assembly 26 at the end of the second light path 24. Accordingly, the photomultiplier tube assembly 26 ideally responds only to photons emitted by atoms of a gas to be detected and does not respond in any substantial way to the excitation light emitted by the excitation fluorescent lamp 14.

The amount of excitation light which reaches the optical filter 18 and photomultiplier tube assembly 26 is minimized by using a light absorbing material for the optics block 12 and by dimensioning the first light path 22 and the cell 16 so that excitation light, for the most part, cannot be scattered by the optics block 12 in such a way that excitation light reaches the optical filter 18 and the photomultiplier tube assembly 26.

While the optics block 12 may be configured so that ideally it cannot scatter light to the optical filter 18 and the photomultiplier tube assembly 26, some light scattering may still exist. For example, there may be some slight background scattering due to the gas atoms in the cell 16. The fluorescent spectrophotometer system 10 has a detection limit which is a function, in part, of the amount of such background scattering. In view of this detection limit, if the amount of light produced by the photons excited from the atoms of a gas to be detected is below the detection limit of the fluorescent spectrophotometer system 10, the photons cannot be measured. Thus, the detection limit is a limit on the detection capability of the fluorescent spectrophotometer system 10. That is, the average intensity of the fluorescence resulting from excitation of the atoms of a gas to be detected must exceed the detection limit of the fluorescent spectrophotometer system 10 if the number of atoms of a gas to be detected in the cell 16 is to be accurately measured.

As can be seen by the following discussion, the detection limit of the fluorescent spectrophotometer system 10 can be neither improved nor degraded by increasing the amount of light supplied to the cell 16 by the excitation fluorescent lamp 14. The intensity of background scattering due to the gas atoms in the cell 16 is proportional to the density of the gas atoms in the cell 16. The intensity of the background scattering is also proportional to the intensity of the excitation light entering the cell 16. Moreover, if the excitation light emitted by the excitation fluorescent lamp 14 fluctuates, then the background scattering also fluctuates. If the fluctuation in the excitation light emitted by the excitation fluorescent lamp 14 is a certain fraction of the average excitation light emitted by the excitation fluorescent lamp 14, then the resulting fluctuation in background scattering is proportional to the intensity of excitation light entering the cell 16.

Furthermore, the intensity of fluorescence is proportional both to the density of atoms of the gas to be detected in the cell 16 and to the intensity of the excitation light entering the cell 16. If the excitation light emitted by the excitation fluorescent lamp 14 fluctuates, then the intensity of fluorescence also fluctuates. Since both the fluctuation in the intensity of background scattering and the intensity of fluorescence are proportional to the average incident intensity, their ratio is independent of the average incident intensity. Therefore, the detection limit, which can be expressed in terms of sample atom density $D_L$ (i.e., the ratio of the total number of gas atoms in the cell 16 to the number of fluorescing atoms in the cell 16) and which is a function of the ratio of the fluctuation in the intensity of background scattering to the intensity of fluorescence, is completely independent of the average excitation intensity.

This detection limit may be defined by the following equation:

$$D_L = \frac{3S\sigma}{F} \quad (2)$$

where $\sigma$ is the normalized standard deviation of the excitation intensity fluctuations, S is the fraction of excitation light scattered to the optical filter 18 and the photomultiplier tube assembly 26, and F is a factor relating to the intensity of fluorescence. $\sigma$ is normalized in that it gives the actual standard deviation of excitation intensity fluctuations when multiplied by the average excitation intensity. The factor F depends on the fluorescence efficiency per atom and the fraction of photons which reach the photomultiplier tube assembly 26. Thus, at the photomultiplier tube assembly 26, the factor S represents scattered light, and the factor F represents the intensity of the photons emitted by the atoms of interest in response to the excitation light supplied by the excitation fluorescent lamp 14.

Because the intensity of the excitation light emitted by the excitation fluorescent lamp 14 fluctuates about an average value, the scattered light also fluctuates. Statistically, this fluctuation may be defined as the standard deviation σ. The fluctuation standard deviation σ is made small by controlling the temperature of the excitation fluorescent lamp 14 and by regulating the power to the excitation fluorescent lamp 14. The detection limit $D_L$ may be improved by decreasing σ. Similarly, the detection limit $D_L$ may be improved by decreasing the background scattering factor S and by increasing the fluorescent intensity factor F.

The background scattering has two types of contributions, i.e. contributions due to the gas sample and optical contributions. As to contributions due to the gas sample, the gas sample, and possible contaminants therein, can have two effects which introduce artifacts in fluorescence measurements. These artifacts are background scattering due to turbidity and fluorescence due to contaminants. Contaminant florescence requires that the contaminant absorb light at wavelengths produced by the excitation fluorescent lamp 14, and that the photons emitted by the contaminant be within the bandpass of the optical filter 18. These requirements greatly restrict the number of contaminants that can potentially generate fluorescence artifacts. Use of the correct filter for the optical filter 18, and/or removal of contaminants from the gas sample, can minimize the impact of these artifacts, if they are present.

Background scattering due to turbidity depends on the composition of the gas in the cell 16. This type of background scattering is practically unavoidable; however, its magnitude is small and, if desired, this magnitude may be established so that its effect can be removed from the final measurements results, as discussed above.

Therefore, if contaminants are not present, the dominant contribution to background scattering is optical. That is, the dominant contribution to background scattering comes from the cell 16 and the optics block 12. Scattering by the optics block 12 depends both upon the reflectivity of the material used for the optics block 12 and upon the geometry of the optics block 12. Scattering by the cell 16 depends upon fabrication of the cell 16 and upon the geometry of the cell 16.

If the optics block 12 were completely reflective, all light entering the first light path 22 from the excitation fluorescent lamp 14 would emerge into the cell 16. On average, the intensity distribution of the light entering the first light path 22 would be the intensity distribution of the light exiting the first light path 22. Thus, in this case, the light which enters the cell 16 would be distributed over all angles from zero to 90° from normal. Light having this distribution would enter the second light path 24. Thus, scattering could not be readily controlled.

One means of avoiding this reflection and scattering is to use a lens to focus and direct the excitation light so that it does not strike the optics block 12. However, lenses add cost and complexity. instead of using a lens, an absorptive material may be used for the optics block 12. Anodized aluminum, for example, although somewhat reflective, is for the most part absorptive. If it is assumed that the light striking the material of the optics block 12 will not reflect, the amount of emitted excitation light which is scattered so that it reaches the optical filter 18 and photomultiplier tube assembly 26 is minimized by controlling the geometry of the first light path 22 and the cell 16.

Figure 6:
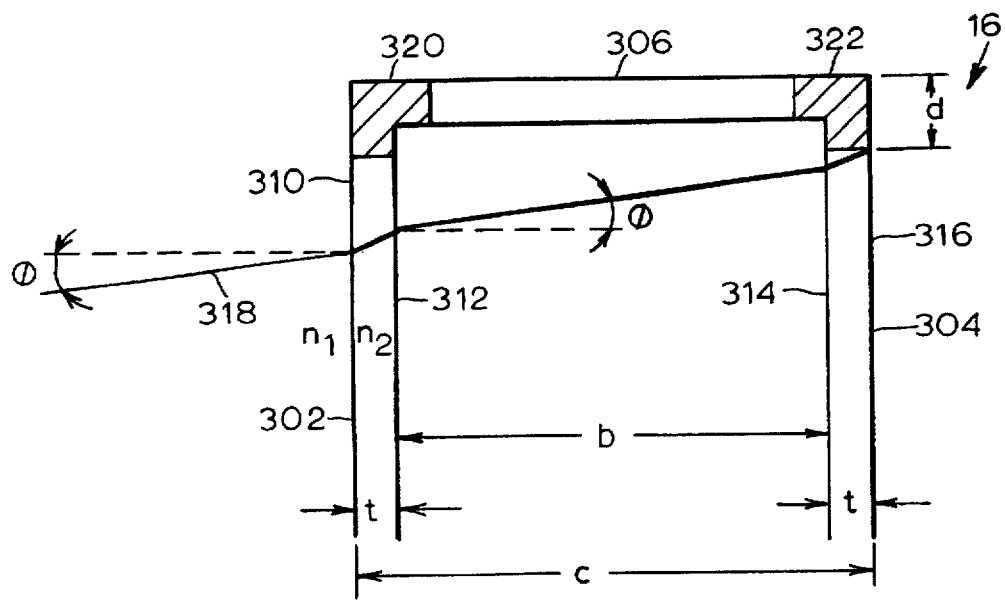
FIGS. 6 and 7 are useful to illustrate the dimensional relationship between a cell of the optics block and the light path through the optics block from an excitation lamp to the cell.
Figure 7:
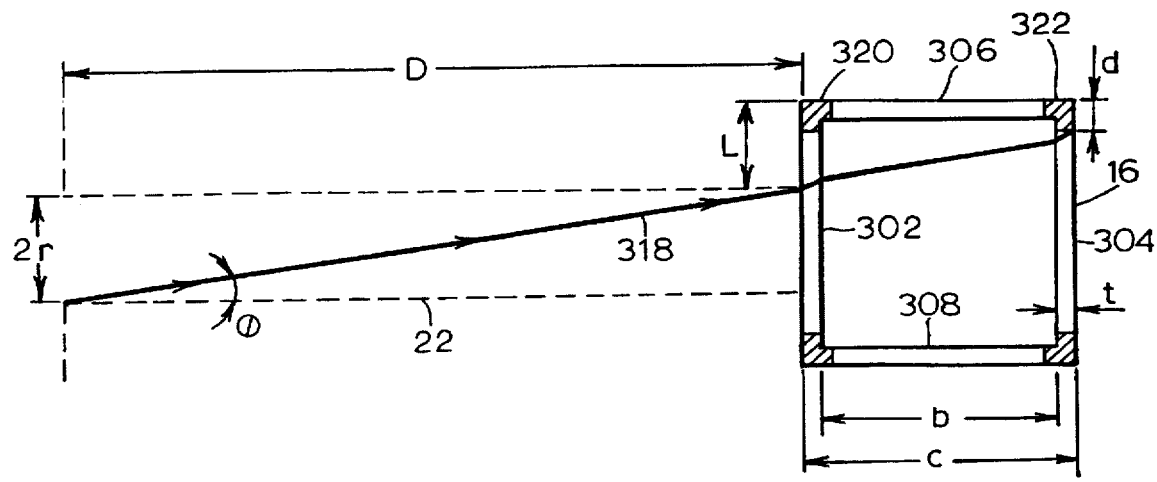

The cell 16 is shown in FIGS. 6 and 7. The cell 16 has a front window 302 nearest to the excitation fluorescent lamp 14, a rear window 304 farthest from the excitation fluorescent lamp 14, and side windows 306 and 308. (These windows may also be referred to herein as walls.) The front window 302 has a front face 310 and a rear face 312.

Similarly, the rear window 304 has a front face 314 and a rear face 316. The front face 310 and the rear face 312 of the front window 302 are separated by a thickness t, and the front face 314 and the rear face 316 of the rear window 304 are also separated by the thickness t. A distance b separates the rear face 312 of the front window 302 and the front face 314 of the rear window 304. The distance b, when added to twice the thickness t, yields the outside distance c between the front face 310 of the front window 302 and the rear face 316 of the rear window 304. The outside distance c may also be referred to as the total width or width of a cell window, such as the side window 308. The first light path has an index of refraction $n_1$, and the quartz of the cell 16 has an index of refraction $n_2$.

A ray of light 318 from the excitation fluorescent lamp 14 travels a distance D along the first light path 22 to the cell 16 and impinges upon the front face 310 of the front window 302 a distance L from the side window 306. The first light path 22 has width 2r. Because of the difference in the indices of refraction $n_1$ and $n_2$, the ray of light 318 is refracted at the front face 310 and again at the rear face 312 of the front window 302 of the cell 16, and emerges from the front window 302 of the cell 16 at its original angle ø. The angle ø is the maximum angle that a ray of light from the excitation fluorescent lamp 14 can have and not be absorbed by the optics block 12. The rear window 304 again refracts the ray of light 318 at its front face 314.

The cell 16 is shown with shaded corners 320 and 322. Along the rear face 316 of the rear window 304, the shading extends a distance d. These shaded corners 320 and 322 are intended to illustrate the critical scattering regions of the cell 16. That is, when a cell such as the cell 16 is manufactured, the corners of the cell represented by the shading shown in FIG. 6 are nonuniform regions which affect light entering therein in an unpredictable manner. That is, light entering these regions scatters unpredictably. Accordingly, these shaded regions of the windows 302, 304, 306, and 308 are referred to herein as diffuse regions. By contrast, the unshaded regions of the windows 302, 304, 306, and 308 are regions of predictability. Light entering these regions transmits therethrough in a predictable manner. Accordingly, these regions are referred to herein as specular regions or as the specular widths of the corresponding windows.

Thus, if the ray of light 318 enters the cell 16 at an angle ø and impinges upon the diffuse region shown as the shaded corner 322, the ray of light 318 may be scattered by this diffuse region so that the ray of light 318 enters the second light path 24 and, if so, will reach the photomultiplier tube assembly 26. On the other hand, if the ray of light 318 enters the cell 16 at an angle ø and does not impinge upon the diffuse region shown as the shaded corner 322, the ray of light 318 transmits predictably through the window 304, and that portion of the ray of light 318 which first reflects off of the rear face 316 of the rear window 304 will not scatter into the second light path 24 and will not reach the photomultiplier tube assembly 26. Rays of light entering the cell 16 with angles of incidence less than ø, or with entry points greater than the distance L from the side window 306, will avoid scattering by the shaded corner 322 into the second light path 24.

Since transmission of light through the specular regions of the cell 16 is predictable, dimensions for the optics block 12 may be predictably determined such that, if light exiting the first light path 22 does not directly impinge upon the diffuse regions of the cell 16 and instead directly (i.e., before reflection) impinges only upon the specular regions of the cell 16, substantially no light will be scattered into the second light path 24.

A general condition can be derived relating the dimensions of the cell 16 and of the first light path 22 that ensures that no rays of light impinge upon the diffuse regions, such as the shaded corner 322, of the rear window 304 before reflection. If it is assumed that the refractions by the front window 302 and the rear window 304 of the cell 16 contribute negligible deflection of the ray of light 318, then it can be shown that excitation light from the excitation fluorescent lamp 14 does directly impinge upon the diffuse regions of the rear window 304 of the cell 16 and does not enter the second light path 24 if the geometry of the first light path 22 and the cell 16 satisfy the following equation:

$$r \leq D \frac{(c/2) - d}{(D + 2c)} \quad (3)$$

The condition stated by equation (3) can be rewritten according to the following equation:

$$\frac{\Delta}{D} \leq \frac{f}{(D + 2c)} \quad (4)$$

where $\Delta$ is the width $2r$ of the first light path 22, and f is identical to $c - 2d$ which is defined as the specular width of the rear window 304 of the cell 16. That is, as described above, the specular width f of the rear window 304 of the cell 16 is the non-shaded region of the rear window 304 such that, if light entering the cell 16 reflects only off of the specular width of the rear face 316 of the rear wall 304, the reflected light does not enter, and transmit through, the second light path 24.

With this arrangement, scattering from the diffuse regions of the rear window 304 of the cell 16 is avoided if the ratio of the width $\Delta$ of the first light path 22 to its length D is less than or equal to the ratio of the specular width f of the rear window 304 of the cell 16 to the sum of the length D of the first light path 22 and twice the total width c of a cell window, e.g. the side window 306.

The next most dominant contribution to scattering is from rays of light that reflect from the front face 314 of the rear window 304 to the diffuse regions of the front window 302, one of which is represented in FIG. 6 as the shaded corner 320. The percentage of any ray of light that reflects off of a reflecting interface is determined by the indices of refraction of the materials at the reflecting interface and by the angle of incidence. For quartz/air interfaces, over the range of incidence angles meeting equation (4), only about four percent of the incident light ray is reflected. However, in order to avoid first reflection of light rays from the front face 314 of the rear window 304 to the diffuse regions of the front window 302, equation (4) may be modified to the following equation:

$$r \leq D \frac{(c/2) - d}{(D + 4c)} \quad (5)$$

As in the case of equation (3), the condition stated by equation (5) can be rewritten according to the following equation:

$$\frac{\Delta}{D} \leq \frac{f}{(D + 4c)} \quad (6)$$

That is, scattering from both the diffuse regions of the rear window 304 and the diffuse regions of the front window 302 (on first reflection) is avoided if the ratio of the width $\Delta$ of the first light path 22 to its length D is less than or equal to the ratio of the specular width f of the cell face to the sum of the length D of the first light path 22 and four times the total width c of the cell window, e.g. the side window 306.

Certain modifications may be made to the present invention. For example, instead of providing bores in an optics block to transmit light from the excitation fluorescent lamp 14 to the cell and from the cell 16 to the photomultiplier tube assembly 26, the optics block may be dispensed with all together and light absorbing tubes may instead be used to transmit light from the excitation fluorescent lamp 14 to a stand alone cell 16 and from the stand alone cell 16 to the photomultiplier tube assembly 26. Moreover, a light absorbing material other than anodized aluminum may be used for the optics block 12. Additionally, while the present invention has been described in connection with the detection of atoms of a gas to be analyzed, it should be recognized that at least some parts of the present invention could also be used in connection with the detection of molecules of a substance to be analyzed. Other modifications will occur to those skilled in the art. All such modifications are considered to fall within the scope of the present invention.

We claim:

1. A light transmitter for use in a spectrophotometer comprising:

a first light path of substantially light absorbing material, wherein the first light path has first and second ends, and wherein the first end of the first light path is arranged to receive light;

a cell, wherein the cell is in light receiving communication with the second end of the first light path, wherein the cell is arranged to receive a sample to be analyzed, and wherein the cell has a specular width;

a second light path of substantially light absorbing material, wherein the second light path has first and second ends, and wherein the first end of the second light path is in light receiving communication with the cell; and, wherein the first light path has a length and a width, wherein a ratio of the width and length of the first light path is related to the specular width of the cell so as to inhibit light from the first end of the first light path being scattered by the cell such that scattered light enters the first end of the second light path.

2. The light transmitter of claim 1 wherein:

the cell has a front wall nearest the second end of the first light path, a rear wall farthest from the second end of he first light path, and a side wall extending between the front and rear walls;

the rear wall has the specular width; and, wherein the ratio of the width and length of the first light path is related to the specular width of the cell so that light from the first end of the first light path strikes only the specular width of the rear wall.

3. The light transmitter of claim 1 wherein:

the length of the first light path is between the first and second ends of the first light path;

the width of the first light path is in a direction which is perpendicular to the length of the first light path;

the cell has a front wall nearest the second end of the first light path, a rear wall farthest from the second end of the first light path, and a side wall extending between the front and rear walls;

the side wall has a width;

the rear wall has the specular width;

the ratio of the width and length of the first light path is the width of the first light path to the length of the first light path; and, the width and length of the first light path, the width of the side wall, and the specular width of the rear wall are arranged so that the ratio of the width of the first light path to the length of the first light path is less than or equal to a ratio of the specular width of the rear wall of the cell to a sum of the length of the first light path and twice the width of the side wall of the cell.

4. The light transmitter of claim 1 wherein:

the length of the first light path is between the first and second ends of the first light path;

the width of the first light path is in a direction which is perpendicular to the length of the first light path;

the cell has a front wall nearest the second end of the first light path, a rear wall farthest from the second end of the first light path, and a side wall extending between the front and rear walls;

the side wall has a width;

the rear wall has the specular width;

the ratio of the width and length of the first light path is the width of the first light path to the length of the first light path; and, the width and length of the first light path, the width of the side wall, and the specular width of the rear wall are arranged so that the ratio of the width of the first light path to the length of the first light path is less than or equal to a ratio of the specular width of the rear wall of the cell to a sum of the length of the first light path and four times the width of the side wall of the cell.

5. The light transmitter of claim 1 wherein:

the length of the first light path is between the first and second ends of the first light path;

the width of the first light path is in a direction which is perpendicular to the length of the first light path;

the cell has a front wall nearest the second end of the first light path, a rear wall farthest from the second end of the first light path, and a side wall extending between the front and rear walls;

the front wall, the rear wall, and the side wall have equal widths;

the rear wall has the specular width;

the ratio of the width and length of the first light path is the width of the first light path to the length of the first light path; and, the width and length of the first light path, the width of a wall of the cell, and the specular width of the rear wall are arranged so that the ratio of the width of the first light path to the length of the first light path is less than or equal to a ratio of the specular width of the rear wall of the cell to a sum of the length of the first light path and twice the width of a wall of the cell.

6. The light transmitter of claim 1 wherein:

the length of the first light path is between the first and second ends of the first light path;

the width of the first light path is in a direction which is perpendicular to the length of the first light path;

the cell has a front wall nearest the second end of the first light path, a rear wall farthest from the second end of the first light path, and a side wall extending between the front and rear walls;

the front wall, the rear wall, and the side wall have equal widths;

the rear wall has the specular width;

the ratio of the width and length of the first light path is the width of the first light path to the length of the first light path; and, the width and length of the first light path, the width of a wall of the cell, and the specular width of the rear wall are arranged so that the ratio of the width of the first light path to the length of the first light path is less than or equal to a ratio of the specular width of the rear wall of the cell to a sum of the length of the first light path and four times the width of a wall of the cell.

7. The light transmitter of claim 1 wherein:

the light transmitter further comprises a block of substantially light absorbing material;

the first light path is a first bore in the block;

the first bore has first and second ends;

the first end of the first bore is arranged to receive light;

the cell is in the block;

the cell is arranged to be in light receiving communication with the second end of the first bore;

the second light path is a second bore in the block;

the second bore has a first end in light receiving communication with the cell;

the second bore has a second end; and, wherein the first bore has a length and a width, wherein a ratio of the width and length of the first bore is related to the cell so as to inhibit light from the first end of the first bore being scattered by the cell such that scattered light enters the first end of the second bore.

8. The light transmitter of claim 7 wherein:

the cell has a front wall nearest the second end of the first bore, a rear wall farthest from the second end of the first bore, and a side wall extending between the front and rear walls;

the rear wall has the specular width; and, the ratio of the width and length of the first bore is related to the cell so that light from the first end of the first bore strikes only the specular width of the rear wall.

9. The light transmitter of claim 7 wherein:

the length of the first bore is between the first and second ends of the first bore;

the width of the first bore is in a direction which is perpendicular to the length of the first bore;

the cell has a front wall nearest the second end of the first bore, a rear wall farthest from the second end of the first bore, and a side wall extending between the front and rear walls;

the side wall has a width;

the rear wall has the specular width;

the ratio of the width and length of the first bore is the width of the first bore to the length of the first bore; and, the width and length of the first bore, the width of the side wall, and the specular width of the rear wall are arranged so that the ratio of the width of the first bore to the length of the first bore is less than or equal to a ratio of the specular width of the rear wall of the cell to a sum of the length of the first bore and twice the width of the side wall of the cell.

10. The light transmitter of claim 7 wherein:

the length of the first bore is between the first and second ends of the first bore;

the width of the first bore is in a direction which is perpendicular to the length of the first bore;

the cell has a front wall nearest the second end of the first bore, a rear wall farthest from the second end of the first bore, and a side wall extending between the front and rear walls;

the side wall has a width;

the rear wall has the specular width;

the ratio of the width and length of the first bore is the width of the first bore to the length of the first bore; and, the width and length of the first bore, the width of the side wall, and the specular width of the rear wall are arranged so that the ratio of the width of the first bore to the length of the first bore is less than or equal to a ratio of the specular width of the rear wall of the cell to a sum of the length of the first bore and four times the width of the side wall of the cell.

11. The light transmitter of claim 7 wherein:

the length of the first bore is between the first and second ends of the first bore;

the width of the first bore is in a direction which is perpendicular to the length of the first bore;

the cell has a front wall nearest the second end of the first bore, a rear wall farthest from the second end of the first bore, and a side wall extending between the front and rear walls;

the front wall, the rear wall, and the side wall have equal widths;

the rear wall has the specular width;

the ratio of the width and length of the first bore is the width of the first bore to the length of the first bore; and, the width and length of the first bore, the width of a wall of the cell, and the specular width of the rear wall are arranged so that the ratio of the width of the first bore to the length of the first bore is less than or equal to a ratio of the specular width of the rear wall of the cell to a sum of the length of the first bore and twice the width of a wall of the cell.

12. The light transmitter of claim 7 wherein:

the length of the first bore is between the first and second ends of the first bore;

the width of the first bore is in a direction which is perpendicular to the length of the first bore;

the cell has a front wall nearest the second end of the first bore, a rear wall farthest from the second end of the first bore, and a side wall extending between the front and rear walls;

the front wall, the rear wall, and the side wall have equal widths;

the rear wall has the specular width;

the ratio of the width and length of the first bore is the width of the first bore to the length of the first bore; and, the width and length of the first bore, the width of a wall of the cell, and the specular width of the rear wall are arranged so that the ratio of the width of the first bore to the length of the first bore is less than or equal to a ratio of the specular width of the rear wall of the cell to a sum of the length of the first bore and four times the width of a wall of the cell.

13. The light transmitter of claim 1 wherein the first and second light paths are disposed at a substantially right angle with respect to one another so as to inhibit light from the second end of the first light path directly entering the first end of the second light path.

14. A system for analyzing a sample comprising:

a spectrophotometer having an output, wherein the spectrophotometer receives the sample to be analyzed, wherein the spectrophotometer stimulates the sample in response to an input light, wherein the spectrophotometer provides an analog signal on its output dependent upon the stimulated sample, and wherein the spectrophotometer includes a first light path of substantially light absorbing material, wherein the first light path has first and second ends, and wherein the first end of the first light path is arranged to receive light, a cell being in light receiving communication with the second end of the first light path and being arranged to receive a sample to be analyzed, wherein the cell has a specular width, a second light path of substantially light absorbing material, wherein the second light path has first and second ends, and wherein the first end of the second light path is in light receiving communication with the cell, and wherein the first light path has a length and a width, wherein the width and length of the first light path form a ratio which is related to the specular width of the cell so as to inhibit light from the first end of the first light path being scattered by the cell so that scattered light enters the first end of the second light path;

an analog-to-digital converter having an input and an output, wherein the input of the analog-to-digital converter is connected to the output of the spectrophotometer so as to receive the analog signal on the output of the spectrophotometer, and wherein the analog-to-digital converter converts the analog signal to a digital signal; and, a processor connected to the input of the spectrophotometer and to the analog-to-digital converter, the processor being arranged to process the digital signal so as to analyze the sample and to control calibration of the analog-to-digital converter at a preconditioned level of the input light supplied to the spectrophotometer.

15. The system of claim 14 wherein the processor is arranged to process the digital signal so as to control calibration of the analog-to-digital converter at a preconditioned level of the input signal on the input of the spectrophotometer.

16. The system of claim 14 wherein:

the processor comprises means for controlling calibration of a zero offset of the analog-to-digital converter at substantially a zero level of the input light supplied to the spectrophotometer.

17. The system of claim 15 wherein:

the processor comprises means for controlling calibration of a zero offset of the analog-to-digital converter by deenergizing the input of the spectrophotometer.

18. The system of claim 14 wherein:

the spectrophotometer includes a cell which receives the sample to be analyzed;

the spectrophotometer includes a light source to supply the input light; and, the light source is arranged to supply the input light to the cell.

19. The system of claim 18 wherein:

the processor comprises means for controlling calibration of a zero offset of the analog-to-digital converter by controlling the input light supplied to the spectrophotometer to deenergize the light source.

20. The system of claim 15 wherein:

the spectrophotometer includes a cell which receives the sample to be analyzed;

the spectrophotometer includes a light source to supply the input light;

the light source is arranged to supply the input light to the cell;

the spectrophotometer includes an amplifier for amplifying light from the cell;

the amplifier has an output; and, the output of the spectrophotometer is the output of the amplifier.

21. The system of claim 20 wherein:

the processor comprises means for controlling calibration of a zero offset of the analog-to-digital converter by shutting off the input light supplied to the spectrophotometer.

22. The system of claim 15 wherein:

the spectrophotometer includes a cell which receives a sample to be analyzed;

the spectrophotometer includes a light source to supply the input light;

the light source is arranged to supply the input light to the cell;

the spectrophotometer includes an amplifier for amplifying light from the cell;

the amplifier has an output;

the spectrophotometer has a power input for receiving electrical power; and, the output of the spectrophotometer is the output of the light amplifier.

23. The system of claim 22 wherein:

the processor comprises means for controlling calibration of a zero offset of the analog-to-digital converter (i) by shutting off the input light supplied to the spectrophotometer and (ii) by controlling the electrical power on the power input of the spectrophotometer at substantially a zero level.

24. A system for analyzing a sample comprising:

a light source;

a first light path of substantially light absorbing material, wherein the first light path has first and second ends, and wherein the first end of the first light path is arranged to receive light from the light source;

a cell, wherein the cell is in light receiving communication with the second end of the first light path, wherein the cell receives the sample to be analyzed, and wherein the cell has a specular width;

a second light path of substantially light absorbing material, wherein the second light path has first and second ends, and wherein the first end of the second light path is in light receiving communication with the cell;

wherein the first light path has a length and a width, wherein a ratio of the width and length of the first light path is related to the specular width of the cell so as to inhibit light from the first end of the first light path being scattered by the cell such that scattered light enters the first end of the second light path;

detecting means for detecting light at the second end of the second light path, wherein the detecting means has an output for providing an output signal representing the detected light; and, processing means connected to the light source and to the output of the detecting means for processing the output signal of the detecting means so as to analyze the sample.

25. The system of claim 24 wherein:

the cell has a front wall nearest the second end of the first light path, a rear wall farthest from the second end of the first light path, and a side wall extending between the front and rear walls;

the rear wall has the specular width; and, the ratio of the width and a length of the first light path is related to the specular width of the cell so that light from the first end of the first light path strikes only the specular width of the rear wall.

26. The system of claim 24 wherein:

the length of the first light path is between the first and second ends of the first light path;

the width of the first light path is in a direction which is perpendicular to the length of the first light path;

the cell has a front wall nearest the second end of the first light path, a rear wall farthest from the second end of the first light path, and a side wall extending between the front and rear walls;

the side wall has a width;

the rear wall has the specular width;

the ratio of the width and length of the first light path is the width of the first light path to the length of the first light path; and, the width and length of the first light path, the width of the side wall, and the specular width of the rear wall are arranged so that the ratio of the width of the first light path to the length of the first light path is less than or equal to a ratio of the specular width of the rear wall of the cell to a sum of the length of the first light path and twice the width of the side wall of the cell.

27. The system of claim 24 wherein:

the length of the first light path is between the first and second ends of the first light path;

the width of the first light path is in a direction which is perpendicular to the length of the first light path;

the cell has a front wall nearest the second end of the first light path, a rear wall farthest from the second end of the first light path, and a side wall extending between the front and rear walls;

the side wall has a width;

the rear wall has the specular width;

the ratio of the width and length of the first light path is the width of the first light path to the length of the first light path; and, the width and length of the first light path, the width of the side wall, and the specular width of the rear wall are arranged so that the ratio of the width of the first light path to the length of the first light path is less than or equal to a ratio of the specular width of the rear wall of the cell to a sum of the length of the first light path and four times the width of the side wall of the cell.

28. The system of claim 24 wherein:

the system further comprises a block of substantially light absorbing material;

the first light path is a first bore in the block;

the first bore has first and second ends;

the first end of the first bore is arranged to receive light;

the cell is in the block;

the cell is arranged to be in light receiving communication with the second end of the first bore;

the second light path is a second bore in the block;

the second bore has a first end in light receiving communication with the cell;

the second bore has a second end; and, wherein the first bore has a length and a width, wherein a ratio of the width and length of the first bore is related to the specular width of the cell so as to inhibit light from the first end of the first bore being scattered by the cell such that scattered light enters the first end of the second bore.

29. The system of claim 28 wherein:

the cell has a front wall nearest the second end of the first bore, a rear wall farthest from the second end of the first bore, and a side wall extending between the front and rear walls;

the rear wall has the specular width; and, the ratio of the width and length of the first bore is related to the cell so that light from the first end of the first bore strikes only the specular width of the rear wall.

30. The system of claim 28 wherein:

the length of the first bore is between the first and second ends of the first bore;

the width of the first bore is in a direction which is perpendicular to the length of the first bore;

the cell has a front wall nearest the second end of the first bore, a rear wall farthest from the second end of the first bore, and a side wall extending between the front and rear walls;

the side wall has a width;

the rear wall has the specular width;

the ratio of the width and length of the first bore is the width of the first bore to the length of the first bore; and, the width and length of the first bore, the width of the side wall, and the specular width of the rear wall are arranged so that the ratio of the width of the first bore to the length of the first bore is less than or equal to a ratio of the specular width of the rear wall of the cell to a sum of the length of the first bore and twice the width of the side wall of the cell.

31. The system of claim 28 wherein:

the length of the first bore is between the first and second ends of the first bore;

the width of the first bore is in a direction which is perpendicular to the length of the first bore;

the cell has a front wall nearest the second end of the first bore, a rear wall farthest from the second end of the first bore, and a side wall extending between the front and rear walls;

the side wall has a width;

the rear wall has the specular width;

the ratio of the width and length of the first bore is the width of the first bore to the length of the first bore; and, the width and length of the first bore, the width of the side wall, and the specular width of the rear wall are arranged so that the ratio of the width of the first bore to the length of the first bore is less than or equal to a ratio of the specular width of the rear wall of the cell to a sum of the length of the first bore and four times the width of the side wall of the cell.

32. The system of claim 24 wherein:

the detecting means comprises means for providing an analog signal in response to the light at the second end of the second light path;

the detecting means comprises an analog-to-digital converting means for converting the analog signal to a digital signal; and, the processing means comprises means for controlling calibration of a zero offset of the analog-to-digital converting means by deenergizing the light source.

33. The system of claim 32 wherein:

the cell has a front wall nearest the second end of the first light path, a rear wall farthest from the second end of the first light path, and a side wall extending between the front and rear walls;

the rear wall has the specular width; and, the ratio of the width and length of the first light path is related to the cell so that light from the first end of the first light path strikes only the specular width of the rear wall.

34. The system of claim 32 wherein:

the length of the first light path is between the first and second ends of the first light path;

the width of the first light path is in a direction which is perpendicular to the length of the first light path;

the cell has a front wall nearest the second end of the first light path, a rear wall farthest from the second end of the first light path, and a side wall extending between the front and rear walls;

the side wall has a width;

the rear wall has the specular width;

the ratio of the width and length of the first light path is the width of the first light path to the length of the first light path; and, the width and length of the first light path, the width of the side wall, and the specular width of the rear wall are arranged so that the ratio of the width of the first light path to the length of the first light path is less than or equal to a ratio of the specular width of the rear wall of the cell to a sum of the length of the first light path and twice the width of the side wall of the cell.

35. The system of claim 32 wherein:

the length of the first light path is between the first and second ends of the first light path;

the width of the first light path is in a direction which is perpendicular to the length of the first light path;

the cell has a front wall nearest the second end of the first light path, a rear wall farthest from the second end of the first light path, and a side wall extending between the front and rear walls;

the side wall has a width;

the rear wall has the specular width;

the ratio of the width and length of the first light path is the width of the first light path to the length of the first light path; and, the width and length of the first light path, the width of the side wall, and the specular width of the rear wall are arranged so that the ratio of the width of the first light path to the length of the first light path is less than or equal to a ratio of the specular width of the rear wall of the cell to a sum of the length of the first light path and four times the width of the side wall of the cell.

36. The system of claim 24 wherein:

the detecting means includes a power input for receiving electrical power;

the detecting means comprises means for providing an analog signal on an output which is a function of light received at the second end of the second light path;

the detecting means further comprises an analog-to-digital converting means for converting the analog signal on the output of the detecting means to a digital signal;

the analog-to-digital converting means has an input coupled to the output of the detecting means; and, the processing means comprises means for controlling calibration of a zero offset of the analog-to-digital converting means (i) by deenergizing the light source and (ii) by controlling the electrical power on the power input of the detecting means at a substantially zero level.

37. The system of claim 36 wherein:

the cell has a front wall nearest the second end of the first light path, a rear wall farthest from the second end of the first light path, and a side wall extending between the front and rear walls;

the rear wall has the specular width; and, the ratio of the width and length of the first light path is related to the cell so that light from the first end of the first light path strikes only the specular width of the rear wall.

38. The system of claim 36 wherein:

the length of the first light path is between the first and second ends of the first light path;

the width of the first light path is in a direction which is perpendicular to the length of the first light path;

the cell has a front wall nearest the second end of the first light path, a rear wall farthest from the second end of the first light path, and a side wall extending between the front and rear walls;

the side wall has a width;

the rear wall has the specular width;

the ratio of the width and length of the first light path is the width of the first light path to the length of the first light path; and, the width and length of the first light path, the width of the side wall, and the specular width of the rear wall are arranged so that the ratio of the width of the first light path to the length of the first light path is less than or equal to a ratio of the specular width of the rear wall of the cell to a sum of the length of the first light path and twice the width of the side wall of the cell.

39. The system of claim 36 wherein:

the length of the first light path is between the first and second ends of the first light path;

the width of the first light path is in a direction which is perpendicular to the length of the first light path;

the cell has a front wall nearest the second end of the first light path, a rear wall farthest from the second end of the first light path, and a side wall extending between the front and rear walls;

the side wall has a width;

the rear wall has the specular width;

the ratio of the width and length of the first light path is the width of the first light path to the length of the first light path; and, the width and length of the first light path, the width of the side wall, and the specular width of the rear wall are arranged so that the ratio of the width of the first light path to the length of the first light path is less than or equal to a ratio of the specular width of the rear wall of the cell to a sum of the length of the first light path and four times the width of the side wall of the cell.

40. The system of claim 24 wherein the first and second light paths are disposed at a substantially right angle with respect to one another so as to inhibit light from the second end of the first light path directly entering the first end of the second light path.

41. A light transmitter for use in a spectrophotometer comprising:

a first light path, wherein the first light path has first and second ends, and wherein the first end of the first light path is arranged to receive light;

a cell, wherein the cell is in light receiving communication with the second end of the first light path, wherein the cell is arranged to receive a sample to be analyzed, and wherein the cell has a specular width;

a second light path, wherein the second light path has first and second ends, and wherein the first end of the second light path is in light receiving communication with the cell; and, wherein the first and second light paths are disposed at a substantially right angle with respect to one another so as to inhibit light from the second end of the first light path directly entering the first end of the second light path, wherein the first light path has a length and a width, and wherein a ratio of the width of the first light path to the length of the first light path is related to the specular width of the cell so as to inhibit scattered light in the cell entering the first end of the second light path.

42. The light transmitter of claim 41 wherein:

the length of the first light path is between the first and second ends of the first light path;

the width of the first light path is in a direction which is perpendicular to the length of the first light path;

the cell has a front wall nearest the second end of the first light path, a rear wall farthest from the second end of the first light path, and a side wall extending between the front and rear walls;

the side wall has a width;

the rear wall has the specular width; and, the width and length of the first light path, the width of the side wall, and the specular width of the rear wall are arranged so that the ratio of the width of the first light path to the length of the first light path is less than or equal to a ratio of the specular width of the rear wall of the cell to a sum of the length of the first light path and twice the width of the side wall of the cell.

43. The light transmitter of claim 41 wherein:

the length of the first light path is between the first and second ends of the first light path;

the width of the first light path is in a direction which is perpendicular to the length of the first light path;

the cell has a front wall nearest the second end of the first light path, a rear wall farthest from the second end of the first light path, and a side wall extending between the front and rear walls;

the side wall has a width;

the rear wall has the specular width; and, the width and length of the first light path, the width of the side wall, and the specular width of the rear wall are arranged so that the ratio of the width of the first light path to the length of the first light path is less than or equal to a ratio of the specular width of the rear wall of the cell to a sum of the length of the first light path and four times the width of the side wall of the cell.

* * * * *

UNITED STATES PATENT AND TRADEMARK OFFICE
CERTIFICATE OF CORRECTION

Figure 1B:
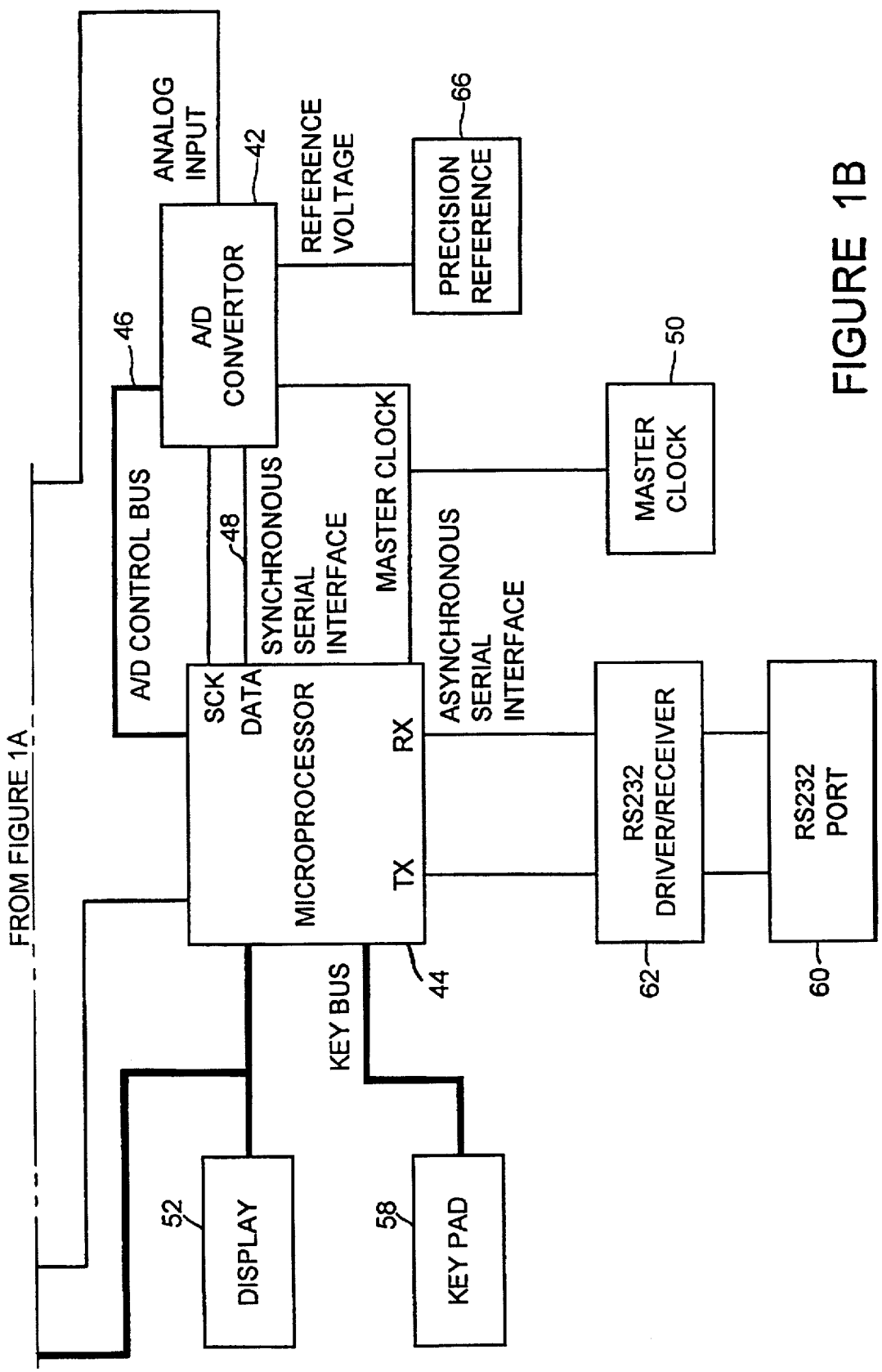

PATENT NO.   : 5,731,873
DATED        : March 24, 1998
INVENTOR(S)  : Brown, et al It is certified that error appears in the above-identified patent and that said Letters Patent is hereby corrected as shown below:

Column 4, line 49, delete " Figure 1 is" and insert -- Figures 1A and 1B, taken together, are --.

Column 4, line 54, delete "Figure 1" and insert -- Figures 1A and 1B --.

Column 4, line 66, delete " Figures 1" and insert -- Figures 1A and 1B --.

Signed and Sealed this

Ninth Day of February, 1999

Attest:

Attesting Officer

*Acting Commissioner of Patents and Trademarks*